United States Patent
Lv et al.

(10) Patent No.: US 11,033,029 B2
(45) Date of Patent: *Jun. 15, 2021

(54) PYRAZOLE AMIDE COMPOUND AND USE THEREOF

(71) Applicant: Shenyang Sinochem Agrochemicals R&D Co., Ltd., Liaoning (CN)

(72) Inventors: Liang Lv, Liaoning (CN); Yugang Li, Liaoning (CN); Zhonggang Shan, Liaoning (CN); Shasha Wu, Liaoning (CN); Bin Wang, Liaoning (CN); Jiyong Liu, Liaoning (CN); Peng Liu, Liaoning (CN); Jizhong Zhou, Liaoning (CN); Huibin Yang, Liaoning (CN); Bin Li, Liaoning (CN)

(73) Assignee: SHENYANG SINOCHEM AGROCHEMICALS R & D CO., LTD., Liaoning (CN)

( * ) Notice: Subject to any disclaimer, the term of this patent is extended or adjusted under 35 U.S.C. 154(b) by 379 days.

This patent is subject to a terminal disclaimer.

(21) Appl. No.: 16/619,409

(22) PCT Filed: Nov. 24, 2014

(86) PCT No.: PCT/CN2014/091998
§ 371 (c)(1),
(2) Date: Dec. 4, 2019

(87) PCT Pub. No.: WO2015/074614
PCT Pub. Date: May 28, 2015

(65) Prior Publication Data
US 2020/0221699 A1     Jul. 16, 2020

(30) Foreign Application Priority Data

Nov. 25, 2013   (CN) .......................... 201310606443.0

(51) Int. Cl.
*A01N 43/56*   (2006.01)
*C07D 231/14*   (2006.01)

(52) U.S. Cl.
CPC ........... *A01N 43/56* (2013.01); *C07D 231/14* (2013.01)

(58) Field of Classification Search
CPC combination set(s) only.
See application file for complete search history.

(56) References Cited

U.S. PATENT DOCUMENTS 7,329,633 B2   2/2008   Dunkel et al.
10,315,998 B2 *   6/2019   Lv .................. C07D 277/56

FOREIGN PATENT DOCUMENTS

| CN | 1639128 A | 7/2005 |
| CN | 1646494 A | 7/2005 |
| CN | 1705668 A | 12/2005 |
| CN | 101115723 A | 1/2008 |
| CN | 100448876 C | 1/2009 |
| CN | 101979375 A | 2/2011 |
| CN | 103391925 A | 11/2013 |
| IN | 388KOLNP2008 A | 8/2008 |
| JP | S62249975 A | 10/1987 |
| JP | 2001302605 A | 10/2001 |
| JP | 2001342179 A | 12/2001 |
| JP | 2004189738 A | 7/2004 |
| WO | 2012065947 A1 | 5/2012 |

OTHER PUBLICATIONS

Patani et al. (Chemical Reviews, 1996, vol. 96, 3147-3176).*
Zhang, Kun et al. Study on synthesis and antifungal activity of 1-methyl-3-difluoromethyl pyrazolamide derivatives; Chinese Journal of Pesticide Science, 2011 vol. 13, No. 6, pp. 576-580.

* cited by examiner

*Primary Examiner* — Kamal A Saeed
(74) *Attorney, Agent, or Firm* — Novick, Kim & Lee, PLLC; Allen Xue

(57) ABSTRACT

Disclosed is a pyrazole amide compound as represented by general formula I, wherein, $R_1$ is selected from hydrogen, $C_1$-$C_4$ alkyl, $C_2$-$C_6$ alkenyl and $C_2$-$C_6$ alkyl; and $R_2$ and $R_3$ can be the same or different, and are respectively and independently selected from the $C_1$-$C_6$ alkyl. The general formula I compound has an excellent bactericidal activity, and can be used to prevent and control fungal diseases.

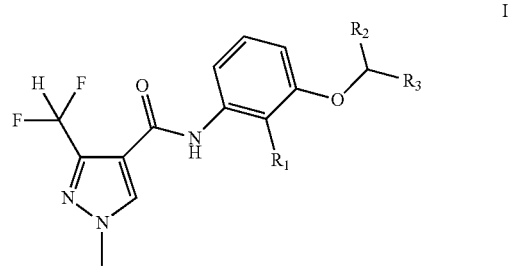

8 Claims, No Drawings

PYRAZOLE AMIDE COMPOUND AND USE THEREOF

FIELD OF THE INVENTION

This invention belongs to the field of fungicide, relates to one kind of pyrazole amide compounds and uses thereof.

BACKGROUND OF THE INVENTION

Novel and improved fungicidal compounds or compositions is continually needed because of the emergence and development of the fungi resistance to the existing fungicides after a period of applications.

The preparation and fungicidal activities of 3-difluoromethtyl-1H-pyrazole-4-carboxamide compounds have been disclosed. For example, *Chinese Journal of Pesticide Science*, 2011, 13(6): 576-580 disclosed the structures and fungicidal activity in vitro of $KC_1$, $KC_2$ and $KC_3$ (compounds of 7g, 7f and 7a in the paper respectively). Compound $KC_4$ was disclosed in CN1646494A(compound 11 in the patent) and has been commercialized as a fungicide, and its common name is bixafen.

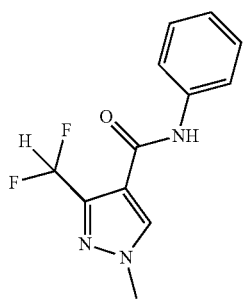

KC₁

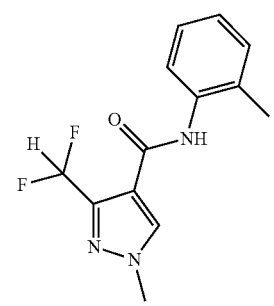

KC₂

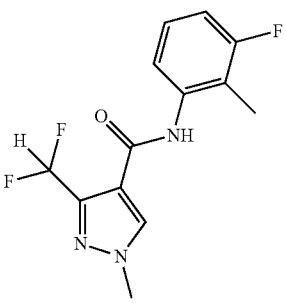

KC₃

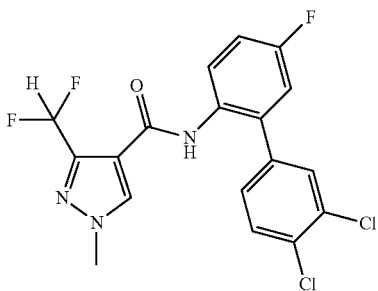

KC₄

There are no compounds according to the present invention are described in state of the arts.

SUMMARY OF THE INVENTION

The purpose of this invention is to provide a kind of novel pyrazole amide compounds with better fungicidal activities, and their applications for controlling disease in agriculture or forestry.

The technical embodiments of this invention are as follows:

A kind of pyrazole amide compounds as represented by the general formula I:

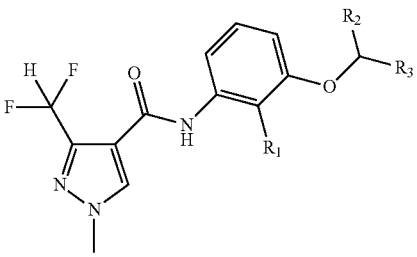

I

Wherein:

$R_1$ is hydrogen, $C_1$-$C_4$-alkyl, ($C_2$-$C_6$ alkenyl)-$C_1$-$C_6$-alkyl;

$R_2$ and $R_3$ may be identical or different, independently of one another represent $C_1$-$C_6$-alkyl.

The preferred compounds of general formula I in this invention are:

$R_1$ is hydrogen, $C_1$-$C_4$-alkyl, ($C_2$-$C_4$-alkenyl)-$C_1$-$C_3$-alkyl;

$R_2$ and $R_3$ may be identical or different, independently of one another represent methyl, ethyl, n-propyl, i-propyl, n-butyl or n-pentyl.

The more preferred compounds of general formula I in this invention are:

$R_1$ is hydrogen, methyl, ethyl, n-propyl, i-propyl, n-butyl, i-butyl, s-butyl or ($C_2$-$C_4$-alkenyl)-$C_1$-$C_3$-alkyl;

$R_2$ is methyl or ethyl;

$R_3$ is methyl, ethyl, n-propyl, i-propyl, n-butyl or n-pentyl.

The more preferred compounds of general formula I in this invention are:

$R_1$ is hydrogen, methyl, i-butyl, allyl, 2-methylallyl, but-3-en-2-yl or 2-methylbut-3-en-2-yl;

$R_2$ is methyl or ethyl;

$R_3$ is methyl, ethyl, n-propyl, n-butyl or n-pentyl

The technical embodiments of this invention also contain the prepared methods of general formula I, each group of formulas are as defined above, unless otherwise specified.

Method I:

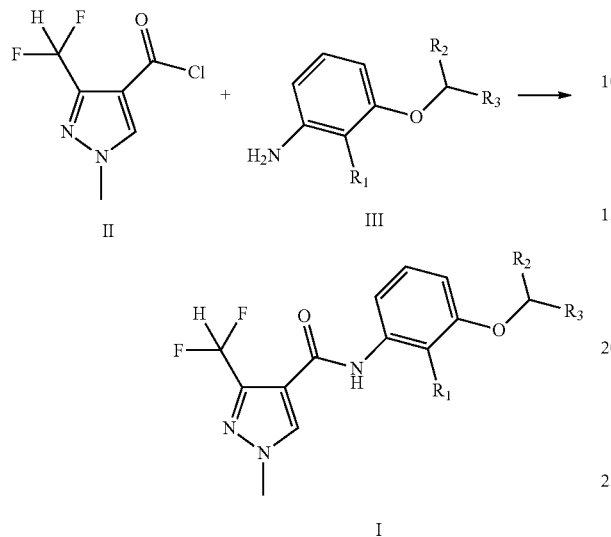

The compounds of general formula II and III are reacted in an appropriate solvent to yield the compounds of general formula I at a certain temperature from −10° C. to boiling point for 30 minutes to 48 hours.

The appropriate solvent is selected from dichloromethane, chloroform, carbon tetrachloride, hexane, benzene, toluene, ethyl acetate, acetonitrile, tetrahydrofuran, dioxane, N, N-dimethylformamide or dimethyl sulfoxide, etc.

Suitable bases include hydrides of alkali metal such as lithium, sodium or potassium, such as sodium hydride, hydroxide of alkali metals such as lithium, sodium or potassium, such as sodium hydroxide, may also be alkali metal carbonates such as sodium carbonate, may also be an organic base such as triethylamine, sodium tert-butoxide, etc.

Compounds of general formula II can be prepared according to the procedures in the CN101979375A.

The compounds of general formula III can be prepared according to the procedures as in the following reference: Bioorganic & Medicinal Chemistry, 2012, 20(3): 1213-1221; Agrochemicals, 2007, 46(5):307-309.

Method II:

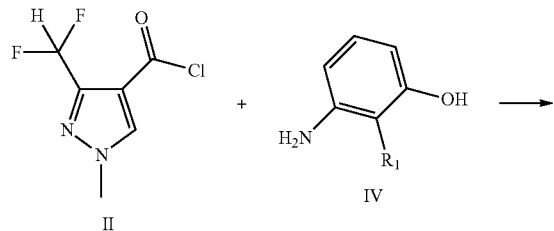

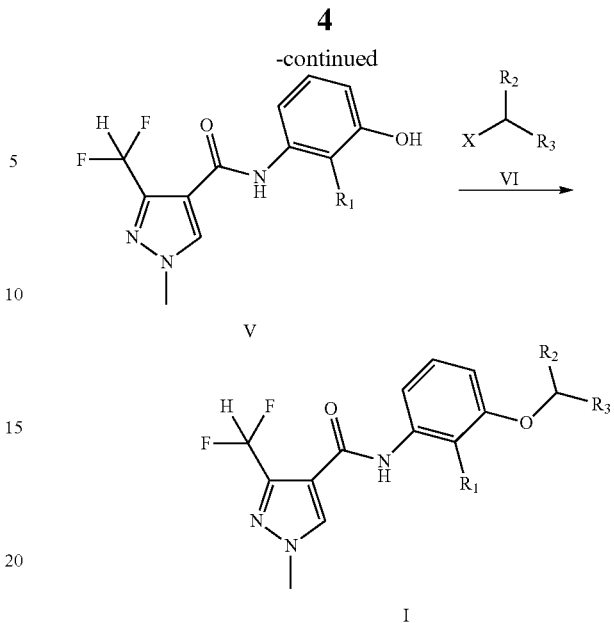

Wherein, X is a halogen.

The compounds of general formula II reacted with IV to yield the compounds of general formula V in an appropriate solvent and in the presence of suitable bases at a certain temperature from −10° C. to boiling point for 0.5 hour to 48 hours.

The appropriate solvent is selected from dichloromethane, chloroform, carbon tetrachloride, hexane, benzene, toluene, ethyl acetate, acetonitrile, tetrahydrofuran, dioxane, N, N-dimethylformamide or dimethyl sulfoxide, etc.

Suitable bases include hydrides of alkali metal such as lithium, sodium or potassium, such as sodium hydride, hydroxide of alkali metals such as lithium, sodium or potassium, such as sodium hydroxide, may also be alkali metal carbonates such as sodium carbonate, may also be an organic base such as triethylamine, sodium tert-butoxide, etc.

The compounds of general formula V reacted with VI (commercially available) to yield the compounds of general formula I in an appropriate solvent and in the presence of suitable bases at a certain temperature from −10° C. to boiling point for 30 minutes to 48 hours.

The appropriate solvent is selected from dichloromethane, chloroform, carbon tetrachloride, hexane, benzene, toluene, ethyl acetate, acetonitrile, tetrahydrofuran, dioxane, N, N-dimethylformamide or dimethyl sulfoxide, etc.

Suitable bases include hydrides of alkali metal such as lithium, sodium or potassium, such as sodium hydride, hydroxide of alkali metals such as lithium, sodium or potassium, such as sodium hydroxide, may also be alkali metal carbonates such as sodium carbonate, may also be an organic base such as triethylamine, sodium tert-butoxide, etc.

The compounds of general formula IV are commercially available or can be prepared refer to the following reference: *Journal of Northwest Normal University* (Natural Science), 2010, 46(5): 59-63.

Table 1 shows the structures and their physical properties of some representative compounds of general formula I:

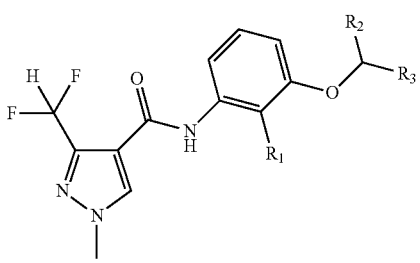

TABLE 1 physical properties of some representative compounds of general formula I

| Compound No. | R₁ | R₂ | R₃ | Appearance (m.p.(° C.)) |
|---|---|---|---|---|
| 1 | H | Me | Me | light yellow solid (89-90) |
| 2 | H | Me | Et | brown oil |
| 3 | H | Me | n-Pr | yellow solid (95-97) |
| 4 | H | Me | i-Pr | |
| 5 | H | Me | n-Bu | |
| 6 | H | Et | Et | white solid (90-91) |
| 7 | Me | Me | Me | yellow solid (86-88) |
| 8 | Me | Me | Et | light yellow solid (104-105) |
| 9 | Me | Me | n-Pr | brown solid (113-114) |
| 10 | Me | Me | n-Bu | yellow oil |
| 11 | Me | Et | Et | brown oil |
| 12 | i-Bu | Me | Me | white solid (128-129) |
| 13 | i-Bu | Me | n-Pr | |
| 14 | i-Bu | Me | n-Bu | |
| 15 | i-Bu | Et | Et | |
| 16 | Allyl | Me | Me | |
| 17 | Allyl | Me | n-Pr | |
| 18 | Allyl | Me | i-Pr | |
| 19 | Allyl | Me | n-Bu | |
| 20 | Allyl | Et | Et | |
| 21 | 2-methylallyl | Me | Me | yellow oil |
| 22 | 2-methylallyl | Me | n-Pr | yellow oil |
| 23 | 2-methylallyl | Me | i-Pr | |
| 24 | 2-methylallyl | Me | n-Bu | |
| 25 | 2-methylallyl | Et | Et | yellow oil |
| 26 | But-3-en-2-yl | Me | Me | |
| 27 | But-3-en-2-yl | Me | n-Pr | |
| 28 | But-3-en-2-yl | Me | i-Pr | |
| 29 | But-3-en-2-yl | Me | n-Bu | |
| 30 | But-3-en-2-yl | Et | Et | |
| 31 | 2-methyl-but-3-en-2-yl | Me | Me | |
| 32 | 2-methyl-but-3-en-2-yl | Me | n-Pr | |
| 33 | 2-methyl-but-3-en-2-yl | Me | i-Pr | |
| 34 | 2-methyl-but-3-en-2-yl | Me | n-Bu | |
| 35 | 2-methyl-but-3-en-2-yl | Et | Et | |

$^1$H NMR (300 MHz, CDCl$_3$) data of representative compounds: Compound 1: 8.09 (br. s, 1H), 7.99 (s, 1H), 7.33-7.34 (m, 1H), 7.19-7.25 (m, 1H), 7.03-7.06 (m, 1H), 6.91 (t, 1H), 6.65-6.69 (dd, 1H), 4.55-4.59 (m, 1H), 3.92 (s, 1H), 1.28 (d, 6H).

Compound 2: 8.13 (s, 1H), 7.98 (s, 1H), 7.33-7.34 (t, 1H), 7.19-7.24 (t, 1H), 7.02-7.05 (m, 1H), 6.91 (t, 1H), 6.66-6.69 (m, 1H), 4.29-4.35 (m, 1H), 3.92 (s, 3H), 1.59-1.77 (m, 2H), 1.25-1.30 (d, 3H), 0.94-0.99 (t, 3H).

Compound 3: 8.10 (s, 1H), 7.99 (s, 1H), 7.32-7.33 (d, 1H), 7.19-7.24 (m, 1H), 7.03-7.07 (m, 1H), 6.89 (t, 1H), 6.65-6.71 (dd, 1H), 4.38-4.40 (m, 1H), 3.93 (s, 3H), 1.60-1.71 (m, 2H), 1.47-1.58 (m, 2H), 1.25 (d, 2H), 0.91-0.98 (t, 3H).

Compound 6: 8.17 (s, 1H), 7.99 (s, 1H), 7.35 (s, 1H), 7.19-7.26 (t, 1H), 6.74-7.10 (t, 1H), 7.03-7.06 (d, 1H), 6.66-6.69 (d, 1H), 4.12-4.16 (m, 1H), 3.90 (s, 1H), 1.63-1.73 (m, 4H), 0.88-0.97 (t, 6H).

Compound 7: 8.02 (s, 1H), 7.91 (br s, 1H), 7.53-7.51 (m, 1H), 7.18-7.13 (m, 1H), 6.88 (t, 1H), 6.76-6.73 (m, 1H), 4.51 (m, 1H), 3.95 (s, 3H), 2.16 (s, 3H), 1.30 (d, 6H).

Compound 8: 8.02 (s, 1H), 7.95 (s, 1H), 7.42-7.44 (d, 1H), 7.11-7.16 (t, 1H), 6.92 (t, 1H), 6.71-6.74 (d, 1H), 4.26-4.32 (m, 1H), 3.87 (s, 3H), 2.16 (s, 3H), 1.59-1.80 (m, 2H), 1.20-1.29 (d, 3H), 0.95-1.00 (t, 3H).

Compound 9: 8.06 (s, 1H), 7.95 (s, 1H), 7.40-7.43 (d, 1H), 7.11-7.17 (t, 1H), 6.76-7.17 (t, 1H), 6.72-6.74 (d, 1H), 4.35-4.37 (m, 1H), 3.86 (s, 3H), 2.15 (s, 3H), 1.41-1.55 (m, 4H), 1.27-1.28 (d, 3H), 0.91-0.94 (t, 3H).

Compound 10: 7.99 (s, 1H), 7.94 (s, 1H), 7.47-7.50 (d, 1H), 7.12-7.18 (t, 1H), 6.74-7.07 (t, 1H), 6.70-6.74 (d, 1H), 4.33-4.36 (m, 1H), 3.93 (s, 3H), 2.16 (s, 3H), 1.34-1.73 (m, 6H), 1.25-1.27 (d, 3H), 0.88-0.94 (t, 3H).

Compound 11: 8.05 (s, 1H), 7.97 (s, 1H), 7.40-7.43 (d, 1H), 7.11-7.17 (t, 1H), 6.75-7.27 (t, 1H), 6.70-6.72 (d, 1H), 4.11-4.15 (t, 1H), 3.88 (s, 3H), 2.15 (s, 3H), 1.60-1.73 (m, 4H), 0.93-0.99 (t, 6H).

Compound 12: 7.98 (s, 1H), 7.88 (s, 1H), 7.40-7.43 (d, 1H), 7.13-7.18 (t, 1H), 6.90-7.26 (t, 1H), 6.70-6.73 (d, 1H), 4.53-4.57 (m, 1H), 3.93 (s, 3H), 2.51-2.54 (d, 2H), 1.84-1.89 (m, 1H), 1.27-1.29 (d, 6H), 0.89-0.93 (d, 6H).

Compound 21: 7.83 (br s, 2H), 7.52-7.55 (d, 1H), 7.17-7.22 (t, 1H), 6.83-7.26 (t, 1H), 6.74-6.77 (d, 1H), 4.79 (s, 1H), 4.52-4.55 (m, 2H), 3.95 (s, 3H), 3.42 (s, 2H), 1.69 (s, 3H), 1.29-1.32 (d, 6H).

Compound 22: 7.83 (s, 2H), 7.52-7.54 (d, 1H), 7.17-7.20 (t, 1H), 6.83-7.23 (t, 1H), 6.72-6.75 (d, 1H), 4.79 (s, 1H), 4.52 (s, 1H), 4.37-4.39 (t, 1H), 3.96 (s, 3H), 3.42 (s, 2H), 1.76 (s, 3H), 1.37-1.58 (m, 4H), 1.24-1.26 (d, 3H), 0.90-0.96 (t, 3H).

Compound 25: 7.84 (s, 2H), 7.50-7.53 (d, 1H), 7.17-7.22 (t, 1H), 6.83-7.16 (t, 1H), 6.70-6.73 (d, 1H), 4.79 (s, 1H), 4.52 (s, 1H), 4.14-4.16 (t, 1H), 3.95 (s, 3H), 3.44 (s, 2H), 1.77 (s, 3H), 1.62-1.71 (m, 4H), 0.90-0.96 (t, 6H).

The pyrazole amide compounds in this invention possess surprisingly high fungicidal activity compared with the known pyrazole amide compounds. So, this invention also provides the use of general formula I compounds for combatting diseases, which can control the disease of oomycetes, ascomycetes, basidiomycetes, deuteromycetes, plasmodiophoromycetes, chytridiomycetes and zygomycetes.

Some fungal diseases which under the class names listed above may be mentioned as example, but not by way of limitation.

Wheat rust, rice sheath blight, wheat sheath blight, cucumber downy mildew, grape downy mildew, wheat powdery mildew, tomato early blight, cucumber anthracnose, rice blast, wheat scab, wheat root rot, watermelon gummy stem blight, scab peanuts, peanut black spot, scab of citrus, tomato late blight, pepper root rot, cotton verticillium wilt, rape blackleg, take-all of wheat, banana leaf spot, wheat scab, pear scab, corn curvalaria leaf spot, cotton fusarium wilt disease, ginseng rust rot, corn leaf blight, stem rot disease of mango, cucumber blight, apple ring rot, apple valsa canker, rape sclertiniose, black leaf streak of banana, glume blight of wheat.

Another embodiment of this invention includes the fungicidal compositions, in which the compounds of general formula I are active ingredients. The weight percentage of active ingredient(s) in the compositions is from 1% to 99%. There are also acceptable carriers in agriculture in these compositions.

The compositions of the present invention can be used in the form of various formulations. Usually, the compounds of general formula I as the active ingredient can be dissolved in or dispersed to carriers or made to a formulation. So that they can be easily dispersed as a fungicide, such as a wettable powder or an emulsifiable concentrate, etc. Therefore, in these compositions, at least a liquid or solid carrier is added, and usually suitable surfactant(s) can be added when needed.

Also provided by this invention are the application methods of controlling diseases, which is to apply the compositions of the present invention to the growing loci of the fungi as above mentioned. The suitably effective dosage of the compounds of the present invention is usually within a range of from 10 g/ha to 1000 g/ha.

For some applications, one or more other fungicides, insecticides, herbicides, plant growth regulators or fertilizer can be added into the fungicidal compositions of the present invention to make additional merits and effects.

DESCRIPTION OF THE INVENTION IN DETAIL

The following synthesis examples and bioassay examples are used to further illustrate the present invention, but not to limit it.

Synthesis Examples

Example 1: Synthesis of Compound 1

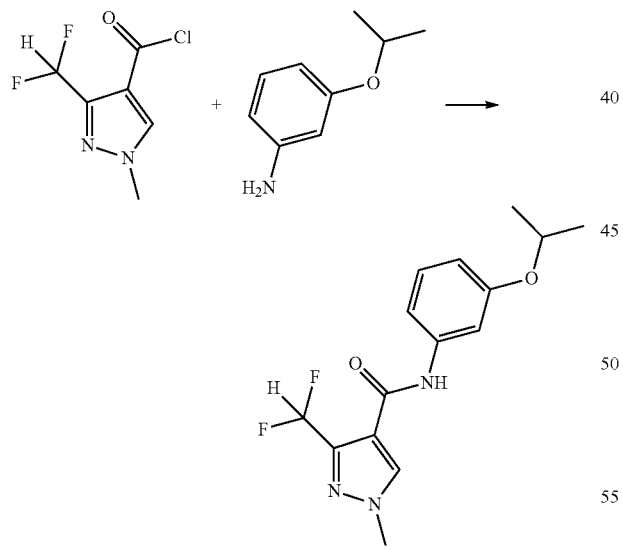

3-isopropoxyaniline (130 mg, 0.85 mmol), triethylamine (90 mg, 0.85 mmol) and dichloromethane (10 mL) were added to a flask, stirred at room temperature, then the solution of 3-(difluoromethyl)-1-methyl-1H-pyrazole-4-carbonyl chloride (170 mg, 0.85 mmol) in dichloromethane (10 mL) was added dropwise. After being stirred for 3 hours at room temperature, water (30 mL) was added. The organic layer was successively washed with saturated sodium bicarbonate solution and saturated brine, dried over anhydrous magnesium sulfate and concentrated by rotary evaporator. The residue was purified by silica gel column chromatography (Fluent: ethyl acetate/petroleum ether=1/2) to give the compound 1 (180 mg) in 68.4% yield.

Example 2: Synthesis of Compound 8

(1) Synthesis of 1-(sec-butoxy)-2-methyl-3-nitrobenzene

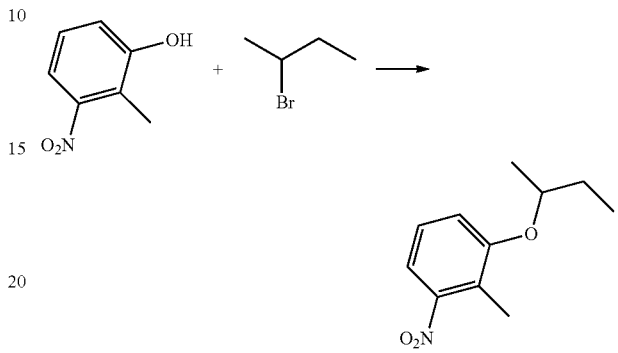

2-bromobutane (2.14 g, 15.17 mmol) and potassium carbonate (2.16 g, 15.17 mmol) were added to the solution of 2-methyl-3-nitrophenol (2.00 g, 13.06 mmol) in N,N-dimethylformamide. The reaction mixture was heated to 90° C. for 2 hours. Then ethyl acetate and water was added, the organic layer was successively washed with saturated brine, dried over anhydrous magnesium sulfate and concentrated by rotary evaporator. The residue was purified by silica gel column chromatography (Fluent: ethyl acetate/petroleum ether=1/100) to give the product (1.65 g) as a solid.

(2) Synthesis of 3-(sec-butoxy)-2-methylaniline

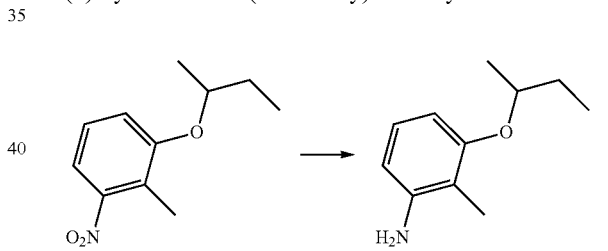

Hydrazine hydrate (5.97 g, 47.76 mmol, 30%) and Palladium on activated carbon(10% Pd)(0.06 g) were added to the solution of 1-(sec-butoxy)-2-methyl-3-nitrobenzene (1.25 g, 5.97 mmol) in ethanol, the reaction mixture was heated to reflux for 2 hours. The mixture was filtered, and then ethyl acetate and water were added to the filtrate. The organic layer was successively washed with saturated brine, dried over anhydrous magnesium sulfate and concentrated by rotary evaporator. The residue was purified by silica gel column chromatography (Fluent: ethyl acetate/petroleum ether=1/10) to give the product (1.02 g) as an oil.

(3) Synthesis of Compound 4

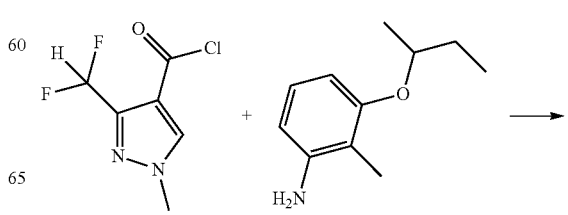

-continued

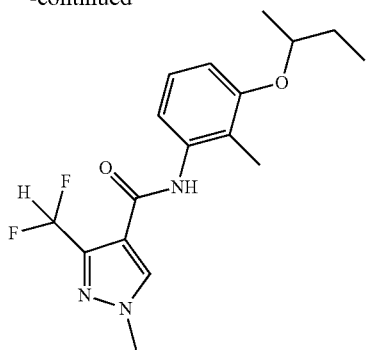

3-(sec-butoxy)-2-methylaniline (240 mg, 1.35 mmol), triethylamine (160 mg, 1.62 mmol) and dichloromethane (10 mL) was added to a flask, stirred at room temperature, then the solution of 3-(difluoromethyl)-1-methyl-1H-pyrazole-4-carbonyl chloride (310 mg, 1.62 mmol) in dichloromethane (10 mL) were added dropwise. After being stirred for 3 hours at room temperatur, water (30 mL) was added. The organic layer was successively washed with saturated sodium bicarbonate solution and saturated brine, dried over anhydrous magnesium sulfate and concentrated by rotary evaporator. The residue was purified by silica gel column chromatography (Fluent: ethyl acetate/petroleum ether=1/2) to give the compound 4 (190 mg) in 43.5% yield.

Example 3: Synthesis of Compound 9

(1) Synthesis of 3-(difluoromethyl)-N-(3-hydroxyphenyl)-1-methyl-1H-pyrazole-4-carboxamide

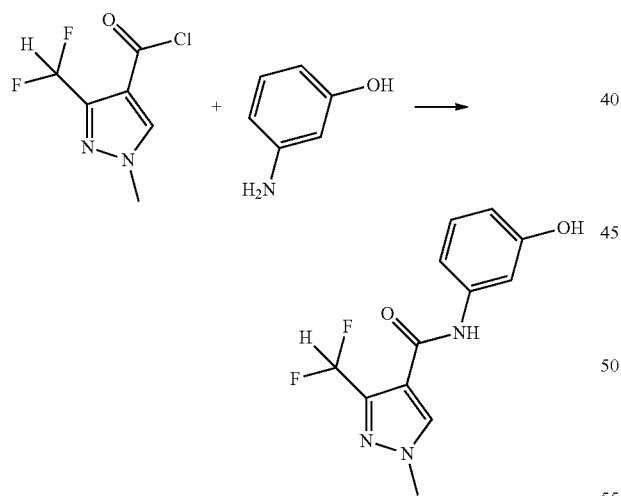

3-aminophenol (1.09 g, 9.99 mmol), triethylamine (1.21 g, 11.99 mmol) and tetrahydrofuran (15 mL) were added to a flask, stirred at room temperature, then the solution of 3-(difluoromethyl)-1-methyl-1H-pyrazole-4-carbonyl chloride (2.33 g, 11.99 mmol) in tetrahydrofuran (15 mL) was added dropwise. After being stirred for 2 hours at room temperatur, ethyl acetate and water was added. The organic layer was successively washed with saturated sodium bicarbonate solution and saturated brine, dried over anhydrous magnesium sulfate and concentrated by rotary evaporator. The residue was purified by silica gel column chromatog- raphy (Fluent: ethyl acetate/petroleum ether=1/2) to give the product (1.48 g) as a white solid.

(2) Synthesis of Compound 9

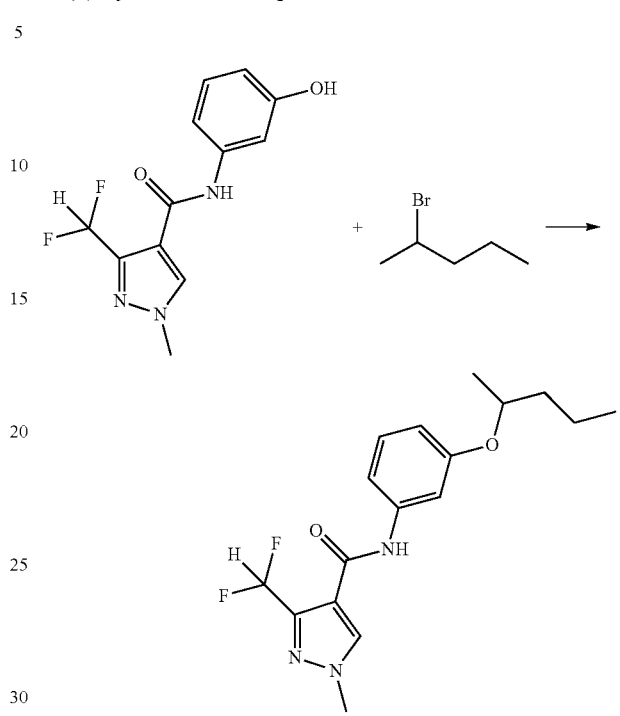

3-(difluoromethyl)-N-(3-hydroxyphenyl)-1-methyl-1H-pyrazole-4-carboxamide (300 mg, 1.12 mmol), potassium carbonate (190 mg, 1.35 mmol), 2-bromopentane (203 mg, 1.35 mmol) and N,N-dimethylformamide (10 mL) were added to a flask, After being stirred for 24 hours at room temperature, ethyl acetate and water was added. The organic layer was successively washed with saturated brine, dried over anhydrous magnesium sulfate and concentrated by rotary evaporator. The residue was purified by silica gel column chromatography (Fluent: ethyl acetate/petroleum ether=1/2) to give the 0.17 g yellow solid in 45.1% yield.

Example 4: Synthesis of Compound 11

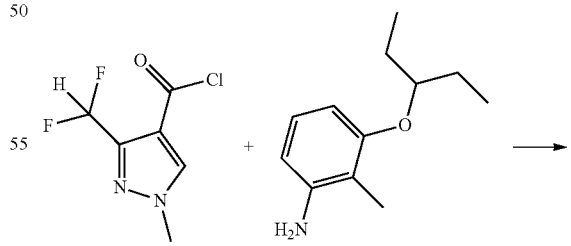

-continued

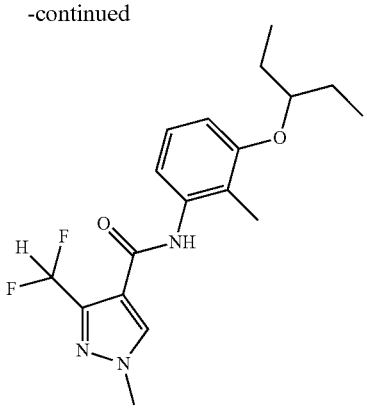

2-methyl-3-(pentan-3-yloxy)aniline (200 mg, 1.03 mmol), triethylamine (125 mg, 1.24 mmol) and dichloromethane (12 mL) were added to a flask, stirred at room temperature, then the solution of 3-(difluoromethyl)-1-methyl-1H-pyrazole-4-carbonyl chloride (241 mg, 1.24 mmol) in dichloromethane (10 mL) were added dropwise. After being stirred for 3 hours at room temperatur, water (30 mL) was added. The organic layer was successively washed with saturated sodium bicarbonate solution and saturated brine, dried over anhydrous magnesium sulfate and concentrated by rotary evaporator. The residue was purified by silica gel column chromatography (Fluent: ethyl acetate/ petroleum ether=1/2) to give 250 mg product in 65.3% yield.

Example 5: Synthesis of Compound 21

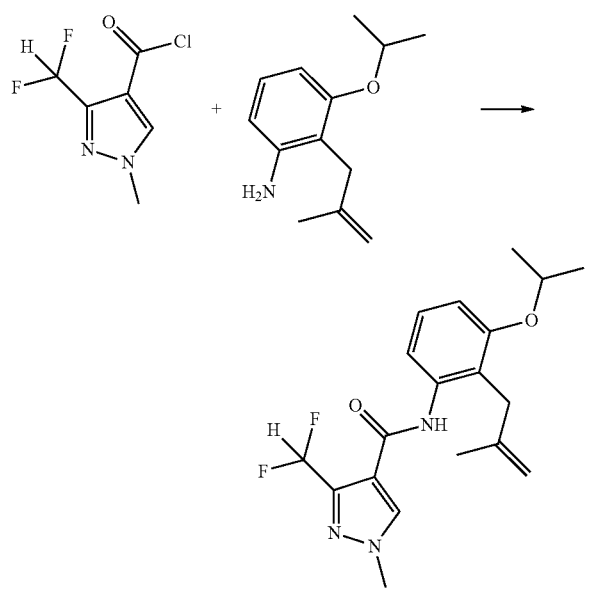

3-isopropoxy-2-(2-methylallyl)aniline (220 mg, 1.07 mmol), triethylamine (130 mg, 1.29 mmol) and dichloromethane (12 mL) were added to a flask, stirred at room temperature, then the solution of 3-(difluoromethyl)-1-methyl-1H-pyrazole-4-carbonyl chloride (250 mg, 1.29 mmol) in dichloromethane (10 mL) were added dropwise. After being stirred for 3 hours at room temperatur. Then water (30 mL) was added, the organic layer was succes-sively washed with saturated sodium bicarbonate solution and saturated brine, dried over anhydrous magnesium sulfate and concentrated by rotary evaporator. The residue was purified by silica gel column chromatography (Fluent: ethyl acetate/petroleum ether=1/3) to give 200 mg product in 46.2% yield.

The compounds of general formula I in the present invention can be prepared by the above-described methods.

Biological Examples

Example 6 Determination of Fungicidal Activity

Fungicidal activity of the compounds in the present invention against many kinds diseases were carried out. The procedure of fungicidal activity determination is as follows:

The fungicidal activity was tested in vivo manner on the potted plants. The test compounds of the present invention were dissolved in proper solvent (choosing the solvent according their dissolving ability to the compounds, the solvents could be acetone, methanol or N,N-dimethylformide, etc. The volume ratio between solvent and liquid sprayed was equal to or less than 0.05) and dilute with water contain 0.1% Tween 80 to given concentrations. Compounds of present invention was sprayed onto the leaves of seedling according to the designed concentration. Meanwhile, water was set as the blank control, three replicates were set for each treatment, the spore suspension were inoculated on the second day after treatment, then the plants were placed in an artificial climate chamber (temperature: day 25° C., night 20° C., relative humidity 95 to 100%). 24 hours later, the plants were moved to green house to cultivated. The plants which not need to control humidity was inoculated spore suspension in green house and cultivated in green house directly. The results were investigated after the plants were fully infected relative to the blank control (usually one week). The test results grading 100-0 refers to the <A Manual of Assessment Keys for Plant Diseases> which edited by American Phytopathological Society. "100" refer to no infection and "0" refer to the most serious infection Some test results were listed as follows:

Protective effect against wheat powdery mildew (Erysiphe graminis DM f. sp. tritici (Em. Marchal)):

According to the test method described above, the following compounds among the test compounds exhibit good fungicidal activity against wheat powdery mildew at 400 ppm, the protective effect was 80% or more: compound 9.

Protective effect against cucumber anthracnose (Colletotrichum orbiculare):

According the test method described above, the following compounds among the test compounds exhibit good fungicidal activity against cucumber anthracnose at 400 ppm, the protective effect was 80% or more: compound 3 and 11.

Protective effect against cucumber downy mildew (Pseudoperonospora cubensis (Berk.et Curt.) Rostov)

According the test method described above, parallel test were carried out between compounds 2 and 11 of present invention and the known compounds $KC_1$, $KC_2$, $KC_3$ and $KC_4$ (they are the compounds 7g, 7f and 7a in Chinese Journal of Pesticide Science, 2011, 13(6): 576-580 and compound of 11 in CN1646494A, respectively). The test results are listed in table 2.

TABLE 2

The parallel protectant activity test result against cucumber downy mildew between compounds 2 and 11 of present invention and the known compounds

| Compound | Control effect against cucumber downy mildew (%) 400 ppm |
|---|---|
| 2 | 100 |
| 11 | 90 |
| $KC_1$ | 0 |
| $KC_2$ | 0 |
| $KC_3$ | 0 |
| $KC_4$ | 0 |

Protective effect against corn rust (*Puccinia sorghi* Schw):

According the test method described above, the following compounds among the test compounds exhibit good fungicidal activity against corn rust at 400 ppm, the protective effect was 80% or more: 1, 2, 3, 7, 9, 11 and 21.

According the test method described above, parallel test were carried out between compounds 1, 3, 7, 9, 11 and 21 of present invention and the known compounds $KC_1$, $KC_2$, $KC_3$ and $KC_4$. The test results are listed in table 3.

TABLE 3

The parallel test of protectant activity against corn rust between some compounds of present invention and the known compounds

| Compounds | Control effect against corn rust (%) | |
|---|---|---|
| | 25 ppm | 6.25 ppm |
| 1 | 100 | 100 |
| 3 | 100 | 95 |
| 7 | 100 | 98 |
| 9 | 100 | 90 |
| 11 | 100 | 90 |
| 21 | 100 | 90 |
| $KC_1$ | 60 | 0 |
| $KC_2$ | 0 | 0 |
| $KC_3$ | 30 | 20 |
| $KC_4$ | 50 | 0 |

The invention claimed is:

1. A pyrazole amide compound of formula I:

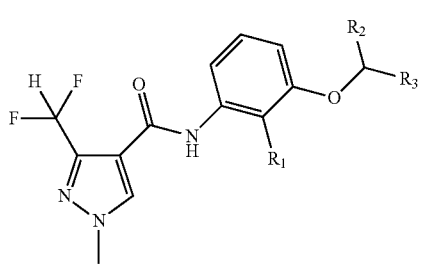

wherein:
$R_1$ is $C_1$-$C_4$ alkyl or ($C_2$-$C_6$ alkenyl)-$C_1$-$C_6$-alkyl; and
$R_2$ and $R_3$ are independently $C_1$-$C_6$ alkyl.

2. The pyrazole amide compound according to claim 1, wherein $R_1$ is $C_1$-$C_4$ alkyl or ($C_2$-$C_4$- alkenyl)-$C_1$-$C_3$-alkyl; and $R_2$ and $R_3$ are independently methyl, ethyl, n-propyl, i-propyl, n-butyl, or n-pentyl.

3. The pyrazole amide compound according to claim 1, wherein $R_1$ is methyl, ethyl, n-propyl, i-propyl, n-butyl, i-butyl, s-butyl, or ($C_2$-$C_4$- alkenyl)-$C_1$-$C_3$-alkyl;

$R_2$ is methyl or ethyl; and $R_3$ is methyl, ethyl, n-propyl, i-propyl, n-butyl, or n-pentyl.

4. The pyrazole amide compound according to claim 1, wherein $R_1$ is methyl, i-butyl, allyl, 2-methylallyl, but-3-en-2-yl, or 2-methylbut-3-en-2-yl;

$R_2$ is methyl or ethyl; and $R_3$ is methyl, ethyl, n-propyl, n-butyl or n-pentyl.

5. A process for preparing a pyrazole amide compound of claim 1, comprises:

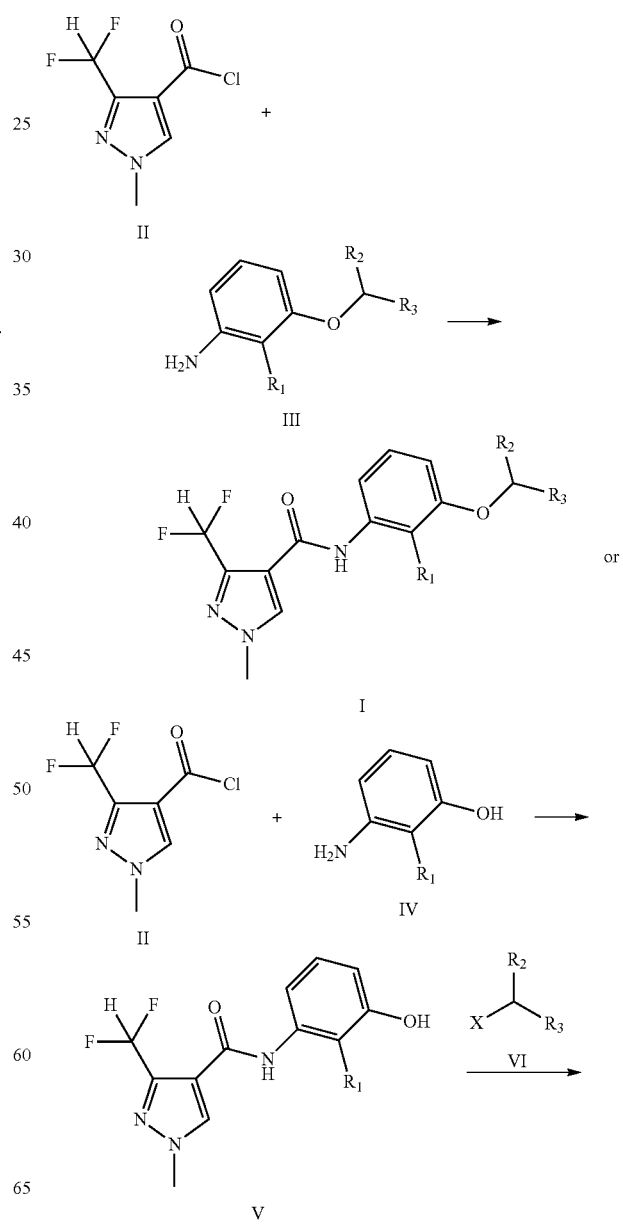

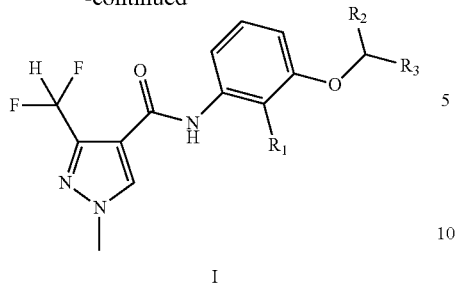

I wherein:
X is a halogen;
$R_1$ is $C_1$-$C_4$ alkyl or ($C_2$-$C_6$- alkenyl)-$C_1$-$C_6$- alkyl;
$R_2$ and $R_3$ are independently $C_1$-$C_6$ alkyl.

6. A method for controlling fungal disease comprising applying a pyrazole amide compound of claim 1.

7. A fungicidal composition, comprising a pyrazole amide compound of claim 1 and a suitable carrier in agriculture or forestry, wherein a weight percentage of the pyrazole amide compound is 1%-99%.

8. A method for controlling diseases, comprising applying the fungicidal composition of claim 7 to the fungi or a habitat thereof with an effective amount in a range of from 10 g/ha to 1000 g/ha.

* * * * *